US008343730B2

(12) United States Patent
Giesen et al.

(10) Patent No.: US 8,343,730 B2
(45) Date of Patent: Jan. 1, 2013

(54) METHOD FOR DETERMINING THE COURSE OF PROTEOLYTIC ACTIVITY

(75) Inventors: Peter L. A. Giesen, Maastricht (NL); Kerry Tappenden, Canterbury (GB); Wynne Jones, Canterbury (GB)

(73) Assignee: Thrombinoscope B.V., BC Maastricht (NL)

( * ) Notice: Subject to any disclaimer, the term of this patent is extended or adjusted under 35 U.S.C. 154(b) by 232 days.

(21) Appl. No.: 12/513,205

(22) PCT Filed: Nov. 2, 2007

(86) PCT No.: PCT/EP2007/009528
§ 371 (c)(1),
(2), (4) Date: Nov. 11, 2009

(87) PCT Pub. No.: WO2008/052795
PCT Pub. Date: May 8, 2008

(65) Prior Publication Data
US 2010/0105091 A1    Apr. 29, 2010

(30) Foreign Application Priority Data

Nov. 2, 2006 (EP) .................................... 06022813

(51) Int. Cl.
*C12Q 1/56* (2006.01)
(52) U.S. Cl. .......................................................... 435/13
(58) Field of Classification Search .............. 435/13, 435/214; 436/69; 73/64.41; 422/73
See application file for complete search history.

(56) References Cited

U.S. PATENT DOCUMENTS

| 6,740,096 | B2 | 5/2004 | Teague et al. | |
|---|---|---|---|---|
| 8,133,696 | B2 | 3/2012 | Giesen et al. | |
| 2006/0051828 | A1* | 3/2006 | Giesen et al. | 435/13 |
| 2009/0311730 | A1* | 12/2009 | Hemker et al. | 435/13 |
| 2012/0135436 | A1 | 5/2012 | Giesen et al. | |

FOREIGN PATENT DOCUMENTS

| WO | 0052199 | 9/2000 |
|---|---|---|
| WO | WO0052199 A1 | 9/2000 |
| WO | 03093831 | 11/2003 |
| WO | WO03093831 A1 | 11/2003 |
| WO | WO2008052795 A1 | 5/2008 |

OTHER PUBLICATIONS

International Search Report PCT/EP2007/009528.
Jones Laurie et al "Quenched BODIPY dye-labeled casein substrates for the assay of protease activity by direct fluorescence measurement" Analytical Biochemistry, Academic Press, San Diego, CA. vol. 251, 1997, pp. 144-152.
NG David et al "Real time in vivo imaging and measurement of serine protease activity in the mouse hippocampus using a dedicated complementary metal-oxide semiconductor of imaging device" Journal of Neuroscience Methods, Elseiver Science Publisher B.V., Amsterdam, NL, vol. 156, No. 1-2. Sep. 2006, pp. 23-30.
Orthner C L et al "Inhibition of human coagulation Factor-XA by Thrombin Substrates". Thrombosis Research, vol. 23, No. 6, 1981, pp. 533-540.
Form PCT/ISA/237—Written Opinion of the international Search Authority, Feb. 6, 2008.
Jones Laurie J. et al: "Quenched BODIPY Dye-Labeled Casein Substrates for the Assay of Protease Activity by Direct Fluorescence Measurement" Analytical Biochemistry, Academic Press, San Diego, CA, US, vol. 251, 1997, pp. 144-152, XP002152059 ISSN: 0003-2697.
Ng David C et al: "Real Time in Vivo Imaging and Measurement of Serine Protease Activity in the Mouse Hippocampus Using a Dedicated Complementary Metal-Oxide Semiconductor Imaging Device" Journal of Neuroscience Methods, Elsevier Science Publisher B.V. Amsterdam, NL, vol. 156, No. 1-2, Sep. 2006, pp. 23-30, XP008076024 ISSN:0165-0270.
Orthner C L et al: "Inhibition O fHuman Coagulation Factor-XA by Thrombin Substrates" Thrombosis Research, vol. 23, No. 6, 1981, pp. 533-540, XP002467868 ISSN: 0049-3848.

* cited by examiner

*Primary Examiner* — Ralph Gitomer
(74) *Attorney, Agent, or Firm* — William D. Schmidt, Esq.; Sorell, Lenna & Schmidt, LLP.

(57) ABSTRACT

A method is provided for determining in real time the course of proteolytic, e.g., thrombin activity, in a sample of clotting blood or plasma. By frequent mixing of a sample, clot formation may be controlled in a dense manner such that the majority of the sample remains fluid. This will inhibit cell precipitation and allow for informative monitoring as signal substrate is added.

20 Claims, 3 Drawing Sheets

METHOD FOR DETERMINING THE COURSE OF PROTEOLYTIC ACTIVITY

This application is a National Stage application filed under Rule 371 based upon PCT/EP07/09528 filed Nov. 2, 2007, which claims priority to application EPO 06022813.7 filed Nov. 2, 2006.

FIELD OF THE INVENTION

The present invention is in the field of diagnostics and relates more particularly to a method for monitoring, in real time, the course of the concentration of biologically active enzymes that are transiently present in blood or other body fluids, and to a kit for use in this method.

BACKGROUND OF THE INVENTION

In body fluids, there exist several physiologically important biochemical systems that act through activation and subsequent inactivation of proteolytic enzymes, such as, in blood, the coagulation system, the fibrinolytic system and the complement system, and in gastro-intestinal juices the digestive enzymes. For the assessment of biological function of these systems it is important to be able to follow the course of such proteolytic activity in time. Such function assessment is of paramount diagnostic importance because disturbances of such systems can lead to fatal diseases like coronary infarction, stroke or fatal bleeding (blood coagulation and fibrinolysis), generalised infections and autoimmune diseases (complement system) or disturbed adsorption of food (gastrointestinal juices).

In methods of determining the thrombin generation in plasma or platelet-rich plasma according to the state of the art, the plasma turns into a gel after several minutes. This is due to the conversion of fibrinogen into insoluble fibrin. This fibrin polymerizes, so that a fibrin-network is formed which, in fact, is the actual clot. This clot is similar to a sponge that contains fluid (i.e. plasma or serum) in which thrombin is generated. During this generation of thrombin the signal substrate is converted into a signal-producing leaving group. Since the gel is relatively transparent it is possible to record the fluorescent signal in time in clotting plasma. However, in case of measurement in whole blood the amount of signal is considerably reduced (typically less than 5% of the amount measured in clear plasma) and any movement of the erythrocytes greatly influences the signal. The fibrin network (the gel) that is formed captures the red blood cells and after a while "clot retraction" occurs that results in inhomogeneity of the gel thereby separating fluid captured inside the gel from fluid that is present outside the fibrin network. Following the picture of the "spongy network", clot retraction results in a situation that is similar to part of the sponge being squeezed out. This has such an influence on the signal that measurement would be almost impossible.

WO 03/093831 describes a suitable technique to measure the activity of thrombin in real time in plasma or platelet-rich plasma. The technique includes the addition of a signal substrate to said biological medium. The proteolytic enzyme is able to convert the substrate, and the leaving group of the substrate can be measured with an appropriate technique. This can be the measurement of fluorescence, optical density, NMR, and the like, the choice of which mainly depends on the nature of the signal. When fluorescence is used, then it is in principle possible to measure in turbid solutions such as platelet-rich plasma or plasma that contains fibrin. Also measurement in whole blood, i.e., plasma containing platelets, white blood cells and erythrocytes, would be possible. However, the presence of red blood cells has a great disturbing impact on the signal.

Therefore, there is still a need for a method for measuring the thrombin generation in real time in whole blood in a reliable and simple manner. The present invention provides such a method.

SUMMARY OF THE INVENTION

We have now surprisingly found that when the measurement of proteolytic activity, in particular thrombin activity, substantially as described in WO 03/093831 is carried out in clotting blood or plasma under frequent mixing conditions, the clot will not be formed as a gel but as a much denser clot thereby leaving substantially all fluid outside the fibrin network.

Accordingly, in one aspect of the present invention a method is provided for determining in real time the course of proteolytic activity, in particular thrombin activity, in a sample of clotting blood or plasma or other body fluid as it appears in and disappears from the sample, which comprises the following steps:

a) adding a signal substrate to said sample, said signal substrate causing a detectable signal related to the amount of conversion product formed upon reaction by the generated proteolytic activity, b1) monitoring the signal development in time in said sample to provide a curve, and c1) mixing said sample frequently so that clot formation occurs in a dense manner such that the majority of the sample remains fluid and that cell precipitation is inhibited, wherein said steps b1) and c1) are repeated and performed in an alternate way.

In a particular and preferred embodiment said method comprises the following additional and alternative steps:

d) adding a means with a constant known stable proteolytic activity on the signal substrate as defined in step a) but otherwise inert, to a second parallel sample in which no proteolytic activity is triggered, e) adding the same signal substrate as defined in step a) to step d), said signal substrate causing a detectable signal upon reaction by the means with known stable proteolytic activity, b2) determining the time course of signal development in said first sample and said second parallel sample to provide a curve from each of them, f) comparing said curves to derive the course of proteolytic activity in time in the first sample, and c2) mixing the first and the second sample frequently so that clot formation occurs in said first sample in a dense manner such that the majority of said first sample remains fluid and that cell precipitation in each sample is inhibited, wherein said steps b2) and c2) are repeated and performed in an alternate way.

In another aspect of the invention a kit is provided for carrying out the method of the invention.

These and other aspects will be described in more detail below.

DETAILED DESCRIPTION OF THE INVENTION

Figure 1:
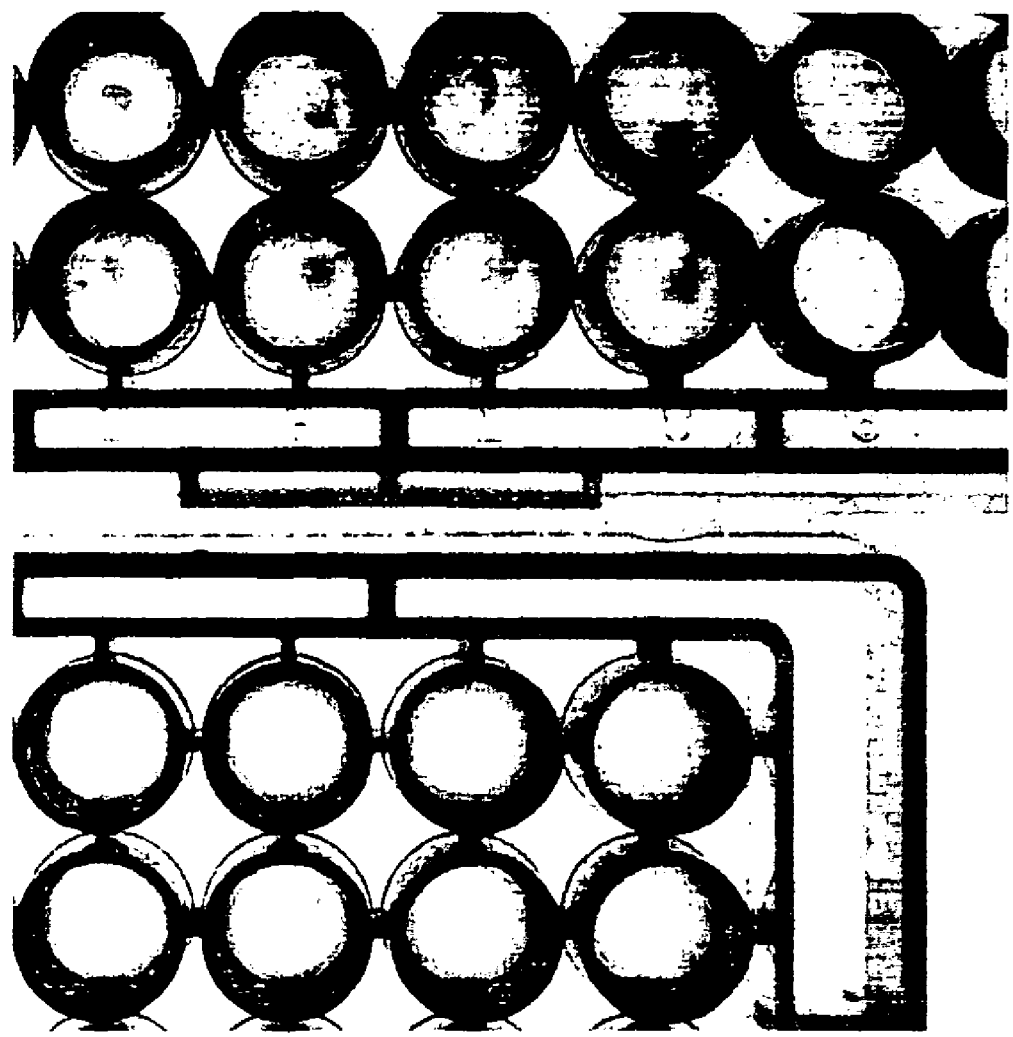
FIG. 1 is a picture taken from a selection of a 96-well plate that was frequently mixed during the formation of the clot (top) and another 96-well plate that was not mixed. In the top picture it is seen that a dense clot is formed in each well. In the bottom picture the clear plasma has turned into a turbid gel. Mixing was done by an orbital shake of 5 seconds that was repeated every 20 seconds. The picture shows an example of what can be assumed will also happen when whole blood is used: under shaking conditions the clot is more dense.

By "frequent mixing conditions", as used herein, we mean moving the container in which the reaction takes place or the fluid within the container such that the fluid and non-fluid substances in the fluid, such as cells, become more uniformly dispersed. Evidently, a substantially uniform dispersion would be the preferred condition. For example, by performing an orbital shake of the container in which thrombin generation takes place, the clot will not be formed as a gel but rather as a much denser clot thereby leaving substantially all fluid outside the network. This can also be achieved by a rotating magnetic stirrer inside the fluid or by another type of stirrer which is known to a person skilled in the art. As a result, the devastating influence of clot retraction on the signal no longer occurs.

The container in which thrombin generation occurs, usually a cuvette, is normally transparent and positioned inside a temperature-controlled apparatus which is able to record the signal produced by the conversion of the substrate. When measurement of fluorescence takes place from the top or the bottom of the container, or cuvette, then precipitation of red blood cells will have an additional disturbing effect on the signal. Measurement from the side of the container instead of from the bottom or top will reduce the influence of precipitation. Alternatively, precipitation can be prevented by mixing repeatedly so that precipitating cells move up again inside the fluid after or during formation of the clot. For instance, a repeated measurement of fluorescent signal within a second each followed by an orbital shake of several seconds is sufficient to carry out a determination of thrombin in whole blood. The drawback of a substantially reduced amount of signal can partly be overcome by choosing optimal wavelengths of the fluorescent probes in combination with favourable positioning of the optical system that receives the fluorescent signal.

The monitoring of the signal development in time in the sample to be measured and the mixing of the sample are repeated and performed in an alternate way until the determination is completed. The whole measurement usually will take from about 10 to 90 minutes. The frequency of the alternate operation of mixing and determining usually amounts from about 3 to 8 times per minute. The mixing usually will take about 3 to 5 seconds each time. The determination usually is in the range of 10-80 milliseconds each time. The method will be fully clear to a person skilled in the art after reading the present description. Further details may be derived in particular from WO 03/093831, which is incorporated herein by reference.

Although the method according to the present invention is particularly suitable for determining in real time the course of proteolytic activity, in particular thrombin activity, in clotting blood or plasma inclusive platelet-rich, platelet-poor or platelet-free plasma, it may also be used in other body fluids which may show clotting activity, for example saliva, serum, urine, cerebrospinal fluid, sperm, and faeces.

The present invention further provides a kit for carrying out the method as set out above. Such a kit conveniently comprises the following components in suitable containers or other conventional packaging means:
a known concentration of $\alpha_2$M-thrombin complex;
a known concentration of thrombin;
a solution containing the leaving group of the signal substrate that is used, the leaving group being capable of producing a signal that can be measured by known techniques, such as fluorescence, optical density, NMR, and the like;
a trigger reagent containing thromboplastin, tissue factor, elagic acid or kaolin, to start the clotting reaction;
an additive facilitating interpretation of the course of thrombin concentration, in particular when specific abnormalities of the hemostatic-thrombotic system are encountered or expected. Suitable additives are, for example, thrombomodulin or activated protein C, which are useful inter alia for the diagnosis of factor V Leiden, or specific antithrombotic or antiplatelet drugs;
a reagent containing a signal substrate;
a software program directly loadable into the memory of a computer for calculatin the thrombin activity curve as determined by the method as defined above, when said program is run on a computer;
an instruction manual.

The kit may suitably comprise freeze-dried reagents.

The invention is further illustrated by the following examples which, however, are not to be construed as limiting the scope of the invention in any respect.

Experimental a. Typical Setup of an Experiment without Internal Calibration

Figure 2:
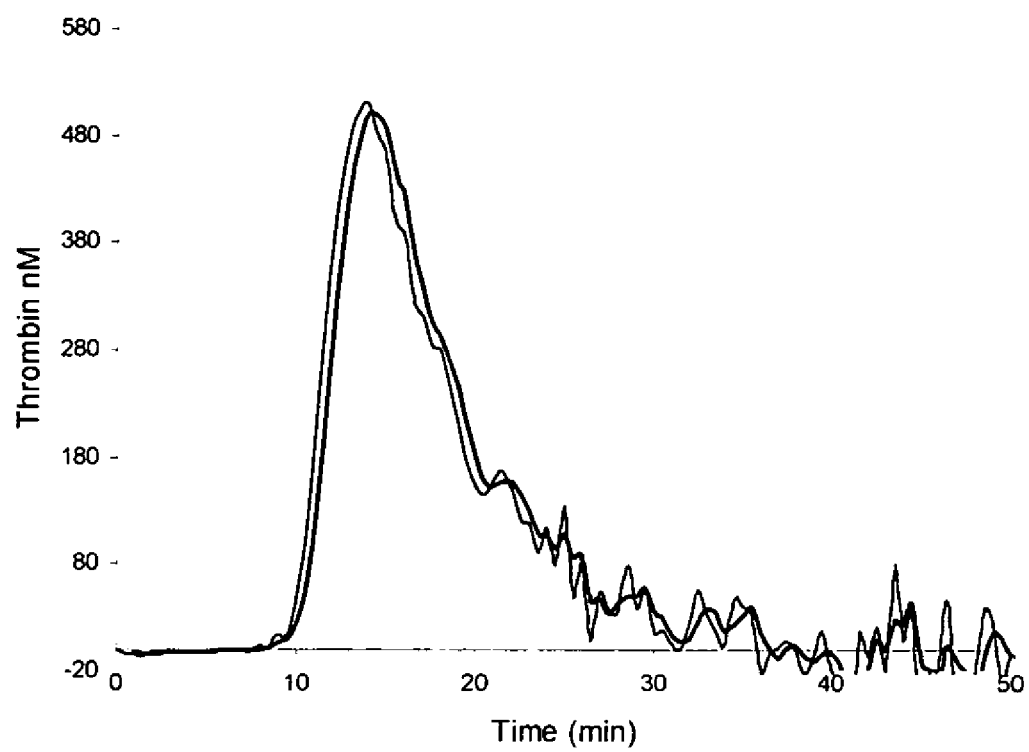
FIG. 2 is a typical example of a measurement of thrombin generation in whole blood. The reaction mixture contained whole blood from a healthy volunteer, as well as 0.5 pM Tissue Factor, fluorogenic substrate (400 µM ZGGR-AMC) and calcium chloride. Fluorescence was measured in a 96-well plate fluorometer and thrombin in time was calculated from the signal.
Figure 3:
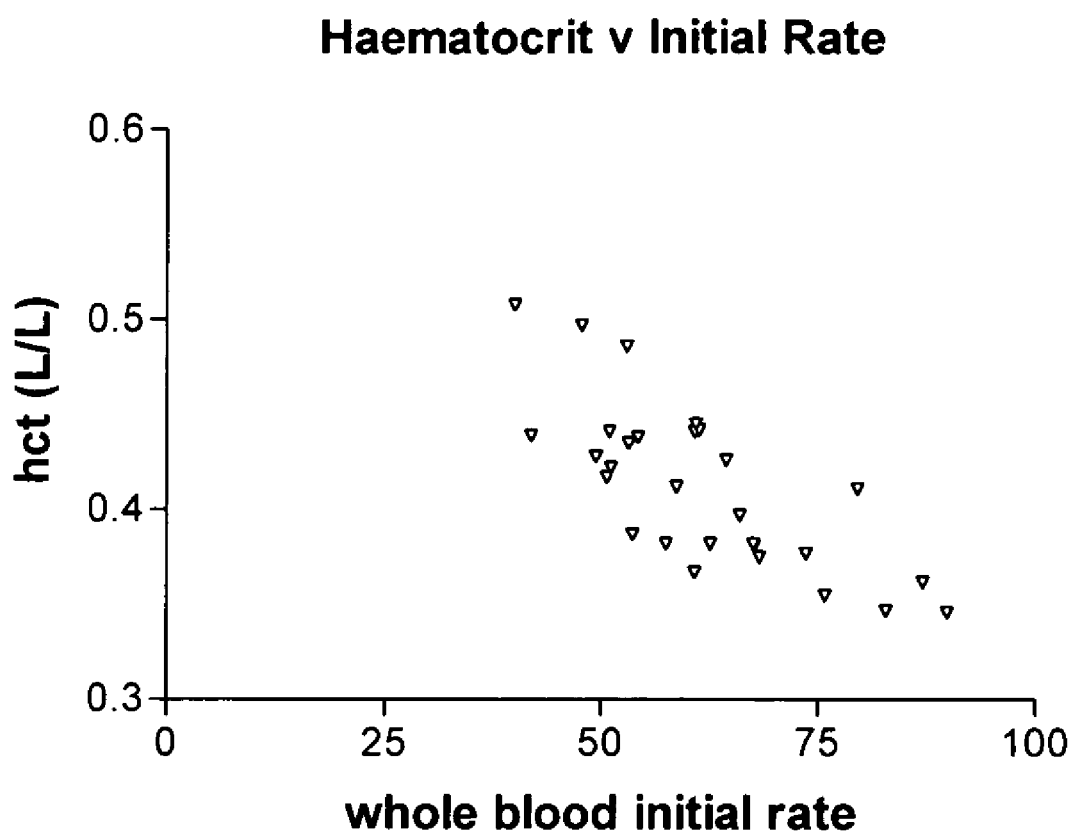
FIG. 3 shows the relationship between initial rate (fluorescent units per minute) of a thrombin calibrator curve and the hematocrit. The thrombin calibrator is a complex of thrombin with alpha2-macroglobulin (α2-M), which is capable of converting the fluorogenic substrate (ZGGR-AMC), but is not inhibited by plasmatic inhibitors of thrombin (such as antithrombin), and it does not participate in the coagulation process. The thrombin calibrator converts the substrate, and the fluorophore that is measured produces a fluorescent signal that is measured in a fluorometer. Although the amount of activity is equal in all samples, the initial rate differs due to the haematocrit (ratio of cell volume and total volume of whole blood). Since the haematocrit differs considerably from donor to donor, the initial rate of the thrombin calibrator can be used to correct for these differences.

Typically, an experiment is performed as follows. Trigger reagent (20 µL) is added to the well of a 96-well plate. The trigger reagent contains a low concentration of Tissue Factor (usually between 0.5 and 20 pM final concentration). Citrated whole blood usually between 50 and 150 µL, in the present example 80 µL, is added and finally the reaction starts after addition of a mixture of fluorogenic substrate (for instance Z-GGR-AMC) and calcium chloride (usually between 200 and 600 µM, and between 14 and 17 mM final concentration, respectively, in the present case 400 µM and 16.7 mM, respectively). After several minutes (lag time) the production of thrombin is started, the concentration goes up until its peak is reached and then comes down again. For a typical curve, see FIG. 2. The first derivative of the fluorescence (measured for instance at 355 nm excitation and 460 nm emission wavelengths) that is followed in time is a reasonable measure of the amount of thrombin in time, although it is recommended to perform additional corrections of the signal in order to properly calculate the concentration of thrombin in time. The nature of these corrections are well known to a person skilled in the art and therefore the correction methods need not to be detailed here.

b. Typical Setup of an Experiment with Internal Calibration

The sample of whole blood is divided into two samples, sample A and sample B. Sample A is added to a well of a 96-well plate that contains trigger (diluted Tissue Factor) and sample B is added to a well that contains a calibrated amount of alpha2-macroglobulin-thrombin complex. This complex has amidolytic activity but cannot be inhibited by plasmatic inhibitors. To both wells fluorogenic substrate is added, sample A will produce thrombin and sample B will not (thrombin production is either inhibited or the citrated sample is not recalcified). From the fluorescence produced in sample B by the conversion of substrate by the calibrated amount of alpha2-macroglobulin-thrombin, the concentration of thrombin in time in sample A can be calculated.

The invention claimed is:

1. A method for determining in real time the course of proteolytic activity in a sample of clotting blood or plasma, the method comprising the following steps:
   a) adding a signal substrate to said sample of clotting blood or plasma in which proteolytic activity is triggered by adding a proteolytic enzyme thereto, said signal substrate causing a detectable signal related to the amount of conversion product formed upon reaction by the proteolytic activity of the proteolytic enzyme,
   b1) monitoring the signal development in time in said sample from a fluid portion of said sample to provide a curve,
   c1) mixing said sample frequently so that a dense clot forms in the sample such that the majority of the sample remains fluid and that cell precipitation is inhibited, wherein said steps b1) and c1) are repeated.

2. A method according to claim 1, wherein the sample is a first sample and said method further comprises:
   d) adding a compound with a constant known stable proteolytic activity on the signal substrate as defined in step a), to a second parallel sample in which no proteolytic activity is triggered,
   e) adding the same signal substrate as defined in step a) to step d), said signal substrate causing a detectable signal upon reaction with the compound, b2) determining the time course of signal development in said second parallel sample to provide a curve,
   f) comparing said curves of b1) and b2) to derive a course of proteolytic activity in time in the first sample, and
   c2) mixing the second sample frequently so that cell precipitation in said second parallel sample is inhibited, wherein said steps b2) and c2) are repeated.

3. A method according to claim 1, wherein the proteolytic activity is selected from the group consisting of activated clotting factor activity, activated fibrinolytic factor activity, and activated component of the complement system activity.

4. A method according to claim 1, wherein the signal substrate comprising a leaving group, wherein said leaving group gives a detectable conversion product upon reaction by the proteolytic enzyme M.

5. A method according to claim 4, wherein the signal substrate is Z-Gly-Gly-Arg-AMC.

6. A method according to claim 4, wherein the detectable conversion product is determined by spectroscopy.

7. A method according to claim 4, wherein the leaving group comprises a fluorescent group, a chromophoric group, or a group releasing hydrogen ions.

8. A method according to claim 1, wherein the conversion product is p-nitroanilide or 7-amino-4-methyl-coumarin.

9. A method according to claim 2, wherein the compound with a constant known stable proteolytic activity is selected from the group consisting of $\alpha_2$-macroglobulin-thrombin complex, staphylocoagulase prothrombin complex, and gamma thrombin.

10. A method according to claim 1, wherein a protease activator is added to said sample prior to adding a signal substrate.

11. A method according to claim 10, wherein the protease activator is selected from the group consisting of calcium ions, phospholipids, Tissue Factor, soluble Tissue factor, thromboplastin, kaolin, and elagic acid.

12. A method according to claim 1, wherein said sample further comprises a pharmaceutical agent.

13. A method according to claim 12, wherein said pharmaceutical agent is being tested for its influence on a haemostatic-thrombotic system.

14. A method according to claim 12, wherein the pharmaceutical agent is an antithrombotic agent.

15. A method according to claim 14, wherein the antithrombotic agent is selected from the group consisting of heparin, dermatan sulphate, a direct thrombin-inhibitor, and a factor Xa inhibitor, a protein C pathway activator or activated protein C.

16. the method according to claim 1, wherein the dectectable signal can be measured by flourescence, optical density, or NMR.

17. The method according to claim 15, wherein the antithrombotic agent is direct thrombin-inhibitor and the direct thrombin-inhibitor is hirudin, argatroban or melagatran.

18. The method according to claim 15, wherein the antithrombotic agent is a factor Xa inhibitor and the factor Xa is thick anticoagulant protein.

19. the method according to claim 15, wherein the antithrombotic agent is a protein C activator and the protein C pathway activator is thrombomodulin.

20. The method according to claim 1, wherein the proteolytic activity is thrombin activity.

* * * * *